United States Patent [19]
Grant et al.

[11] Patent Number: 4,772,262
[45] Date of Patent: Sep. 20, 1988

[54] PORTABLE ELECTRIC BREAST PUMP

[75] Inventors: Elena M. Grant; David N. Grant, Jr., both of Beaverton, Oreg.

[73] Assignee: Natural Technologies, Inc., Beaverton, Oreg.

[21] Appl. No.: 45,708

[22] Filed: Apr. 27, 1987

Related U.S. Application Data

[63] Continuation-in-part of Ser. No. 723,852, Apr. 16, 1985, abandoned.

[51] Int. Cl.$^4$ ............................................. A61M 1/06
[52] U.S. Cl. ...................................................... 604/74
[58] Field of Search ............................ 604/74, 75, 76

[56] References Cited

U.S. PATENT DOCUMENTS

| | | | |
|---|---|---|---|
| 11,135 | 6/1854 | Needham | 604/74 |
| D. 251,015 | 2/1979 | Cone | 604/74 |
| 2,542,505 | 2/1951 | Gascoigne | 604/74 |
| 3,620,408 | 11/1971 | Holbrook | 604/320 |
| 4,323,067 | 4/1982 | Adams | 604/74 |
| 4,583,970 | 4/1986 | Kirchner | 604/74 |
| 4,680,028 | 7/1987 | Stuart | 604/74 |

FOREIGN PATENT DOCUMENTS

| | | | |
|---|---|---|---|
| 2127293 | 4/1984 | United Kingdom | 604/74 |
| 2138686 | 10/1984 | United Kingdom | 604/74 |

Primary Examiner—John D. Yasko
Attorney, Agent, or Firm—Stoel Rives Boley Jones & Grey

[57] ABSTRACT

A breast pump including a vacuum pump, vacuum hose, collection container, and a milk pumping flange for application to a woman's breast for removing milk from the breast, all included within a small carrying case when not in use. The flange includes flexible mouth and throat portions and is generally conical with an elliptical cross section and an interior shape including raised portions simulating the tongue and jaw of a baby. The flange attaches sealingly to a collection container such as a nursing bottle, and vacuum created within the bottle by the pump and hose is applied through the flange to the woman's breast, while a vent opening controls application and release of vacuum. During use the woman can massage her breast through the flexible flange and can control the rhythm with which suction is applied and relaxed, to pump milk more quickly.

5 Claims, 2 Drawing Sheets

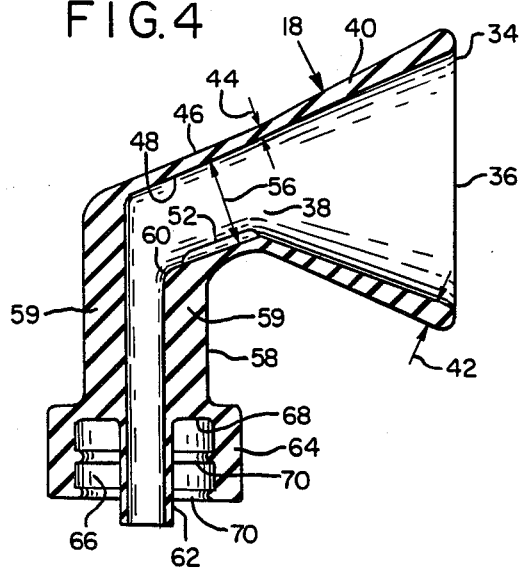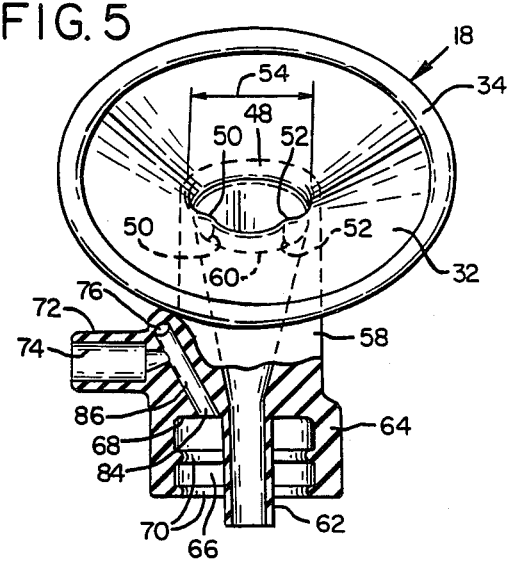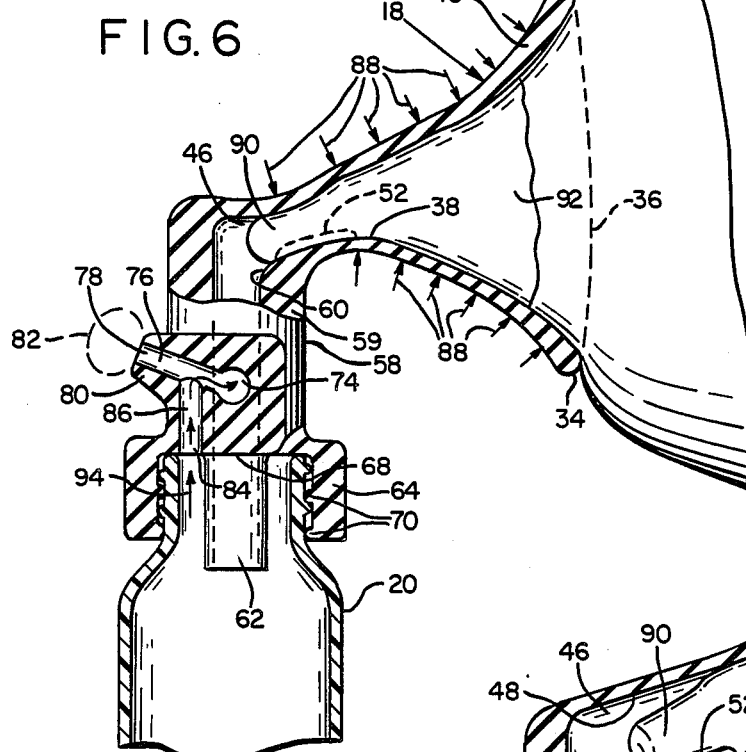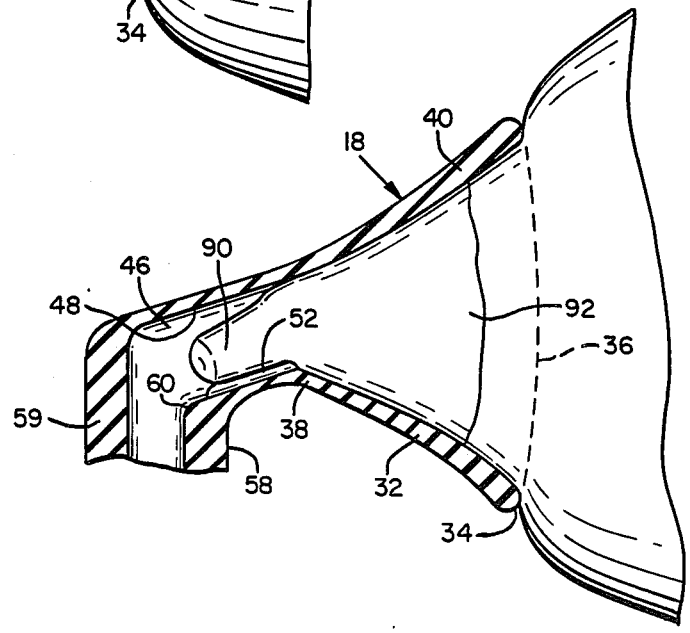

PORTABLE ELECTRIC BREAST PUMP

This is a continuation in part of application Ser. No. 723,852, filed Apr. 16, 1985, now abandoned.

BACKGROUND OF THE INVENTION

The present invention relates to pumps for removing milk from a woman's breast, and particularly to such a pump including a flexible portion for receiving the nipple of the breast in a way which simulates a baby's mouth.

Breast pumps have long been known, but they have, until fairly recently, been used principally in situations where the breast is infected and milk must be withdrawn artificially for a few days, while the infection is present. However, since premature babies have been found to thrive much better when fed human milk than when fed artificial formula milk, many mothers of premature infants have found it desirable to collect their own milk for feeding to their premature babies who are too weak and small to nurse. This may involve a period of several months during which the milk must be artificially withdrawn, because prematurely delivered babies are often hospitalized for three times the length of the time by which they are premature.

The portion of a breast pump which receives the nipple and surrounding portion of the mother's breast in order to suck milk from the breast is called a flange. Previously-known breast pumps have included a flange portion which has been made of a hard material. In some squeeze-bulb hand-operated breast pumps the entire pump, except for the squeeze-bulb, has been made of glass, while disposable hard plastic flanges have been used more recently.

Recently, motorized vacuum pumps have been used to operate as breast pumps. Soxe of these have been similar to the milking machines used for dairy animals, including pulsation control devices which periodically apply and then relieve vacuum in the area inside the flange which is used to receive the nipple and surrounding portion of the woman's breast. In previously-known devices of this type, however, the flange used to receive the nipple and surrounding areola portion of the breast has been of a hard plastics material, and has not very well simulated the natural sucking, squeezing, and massaging of the breast which occurs during natural breast-feeding of an infant. Instead the hard material is likely to slide along the skin of the breast, causing soreness and discomfort.

It is now recognized that the milk produced by a woman's breast is of a different quality when such natural squeezing, sucking, and massaging takes place. The milk produced using the previously known breast pumps of either the hand-operated or mechanically operated types equipped with hard flanges is lower in its content of nutrients than the milk produced when the breast is stimulated naturally by a nursing baby.

Previously-available mechanically-operated breast pumps have included a large vacuum pump which has been portable only with some difficulty. As a result such breast pumps have been rather inconvenient for use by mothers who are not able to remain at home throughout all or most of the day, since a nursing mother ordinarily must relieve the pressure of milk being produced in her breasts every 2-3 hours. Longer time without nursing or pumping the milk from the breasts may soon result in discomfort as the breasts become swollen with the milk contained in them.

Another disadvantage of previously known mechanically-operated breast pumps is that the mechanically-operated pulsation controlling mechanism does not allow a woman to adjust the rate of application and relaxation of suction. Thus the woman is not completely in control of the operation, a factor which leads to an uneasiness which is undesirable for stimulating the let-down and production of milk. Additionally, the vacuum level and capacity of the vacuum pumps of previously-available mechanically-pulsed breast pumps is kept low, in order to prevent tissue damage in case of pulsator malfunction. The withdrawal of milk is therefore slower, using such a breast pump, than when a baby nurses. A nursing baby ordinarily applies a maximum amount of suction very rapidly, and it is this sort of cycle to which the woman physiologically responds best in producing milk. Invariable pulsation rate also prevents a mother using such a breast pump from taking advantage of the larger amounts of milk which can be delivered with each application of suction to the breast at some portions of a period of nursing or breast pumping.

The general result of the various combined disadvantages of previously available mechanical breast pumps is that it takes much longer to pump all of the milk which a breast can produce than it takes for a baby to obtain the same amount of milk by nursing. As a result, a mother is very likely to become tired and stop using the breast pump before delivery of all of the milk produced by the breast at a particular time. This likelihood is further enhanced by irritation of the nipple by the hard, funnel-like flanges previously used. Failure to produce as much milk as desired then often causes psychological problems with milk production, leading to early drying-up of the lactation.

Normally, the period of time during which milk is produced, once let-down has been initiated, is only 7-10 minutes. If all the available milk is not taken within the time of the let-down period, production begins to taper off. Thus, when a breast pump is left in use for too short a period of time for each use, or is incapable of removing all of the milk from the breast, the breast's production begins to decrease, as if a baby were being gradually weaned.

Vacuum pump units for breast pumps, because of their high initial cost and long durability, are usually stocked by such locations as pharmacies, for rental to nursing mothers who need to pump milk from their breasts. However, for the sake of sanitation, the necessary hoses and collection apparatus are normally sold to the mothers. Because there are several different available types of pump mechanisms, it is desirable to have a kit of the necessary additional hoses and collection apparatus which are compatible with all of the readily available pump mechanisms.

What is needed, therefore, is a breast pump which both applies suction and massages at least the areola of a woman's breast during its use, and which, as much as possible, simulates the shape and movement of a baby's mouth and throat, to facilitate pumping the breast milk in a period corresponding more closely to the amount of time which is required for a baby to nurse.

Preferably, such a breast pump should be provided in an easily-portable package, should be controllable in the rate of application of suction and in the number of times suction is applied in a given period of time, and should simulate the feeling, as nearly as possible, of the interior of a baby's mouth and throat on the woman's breast.

SUMMARY OF THE INVENTION

The present invention provides an improved breast pump which is free from the disadvantages and overcomes the shortcomings of the previously-available breast pumps, by providing a compact, easily portable vacuum pump and a breast flange which is of a soft conforming material and which includes a vacuum relief vent permitting the woman using it to manually control the duration, speed of application, and, to some extent, amount of vacuum applied to her breast. The flange according to the invention is flexible, and its interior has a shape simulating the shape of the mouth and throat of a baby, applying pressure to the breast and permitting the woman to massage her breast during use, so that use of the breast pump of the present invention much more closely simulates the nursing of a baby than has previously been possible.

Preferably, a small electrically-powered vacuum pump is mounted within a case the size of a small overnight case. Additional room is available within such a case to carry the other components of the breast pump, including an overflow container and vacuum hoses for connecting between the pump and the overflow container, and from the overflow container to the flexible flange.

The flexible flange includes a flexible collar which fits over the neck of a collection bottle, which may, for example, be an infant's nursing bottle. The flange is of a soft rubber material, and has a thin-walled, flexible, funnel-shaped mouth portion leading into a smaller tubular portion corresponding to the throat and the rearward portion of a baby's mouth. The throat portion of the flange includes structure corresponding to the shape of a baby's tongue and jaw. The throat portion of the flange is connected to a downwardly-extending neck portion whose wall thickness is great enough to provide necessary rigidity to support the mouth and throat portions.

A vacuum hose connection is located in the neck portion and communicates with the collar to apply vacuum to the inside of the collection bottle. A vent communicating with the vacuum tube connection may be covered to create a vacuum within the collection vessel, to draw milk from the mother's breast. As this occurs, air pressure on the outside of the flange presses the flexible walls of the mouth and throat portions of the flange inward toward the breast, squeezing on the area of the breast surrounding the nipple in a manner similar to the way in which a baby squeezes the breast with its mouth. Additionally, the mother can massage the breast using her hand placed on and around the flange.

Preferably, the tube which applies vacuum to the flange of the present invention leads into an overflow container, and a vacuum tube leading from the overflow container to the vacuum pump is equipped with a floating-ball check valve to prevent milk from passing from the overflow container to the pump and causing damage to the pump.

It is therefore a principal object of the present invention to provide an improved breast pump for obtaining milk from a woman's breasts.

It is another important object of the present invention to provide a kit for use with a small vacuum pump for obtaining the milk from a woman's breasts.

It is another object of the present invention to provide a breast pump which closely simulates natural nursing.

It is a principal feature of the present invention that it provides a flange, for contacting a woman's breast, which flange is of a soft pliable material which collapses around the nipple and surrounding portions of the breast in a manner simulating a baby's nursing when vacuum is applied to the interior of the flange.

It is another important feature of the present invention that it includes a vent associated with the flange, which selectively allows entry of air into a milk collection container to relieve vacuum in the flange and thus allow a woman's breast to relax.

Another feature of the invention is that the interior of the throat of the flange includes protrusions shaped to simulate a baby's tongue.

Yet another feature of the invention is the elliptical shape of the funnel-like mouth portion of the flange, which is more similar to a baby's mouth than previously-available flanges for breast pumps.

It is an important advantage of the present invention that the flange has a thin flexible wall which collapses around the portion of a woman's breast which is surrounded by the flange, stimulating the breast to produce milk having higher concentrations of nutrients than milk taken from a breast using suction alone.

Another important advantage of the present invention is that the flange feels more natural than previously available breast pump flanges and results in a woman being able to pump all of the milk from her breast in a shorter time than with previously available breast pumps.

Another significant advantage of the present invention is that the flexible flange of the present invention produces less irritation of the skin of a woman's breast and thus encourages a woman to continue to pump milk until her breast is completely drained, so that lactation is prolonged to a normal duration.

The foregoing and other objectives, features and advantages of the present invention will be more readily understood upon consideration of the following detailed description of the invention taken in conjunction with the accompanying drawings.

BRIEF DESCRIPTION OF THE DRAWINGS

FIG. 4 is a sectional side view of the flange shown in FIG. 2, taken along line 4—4 of FIG. 3.

FIG. 5 is a partially sectional front elevational view of the flange shown in FIG. 2, with the sectional portion of the view taken along line 5—5 of FIG. 2.

FIG. 6 is a sectional side elevational view of the flange and collection container portions of the breast pump shown in FIG. 1, showing the breast pump in use with vacuum applied.

FIG. 7 is a view similar to that of FIG. 6, showing a portion of the flange shown in FIG. 2, with vacuum having been relieved.

DETAILED DESCRIPTION OF THE INVENTION

Figure 1:
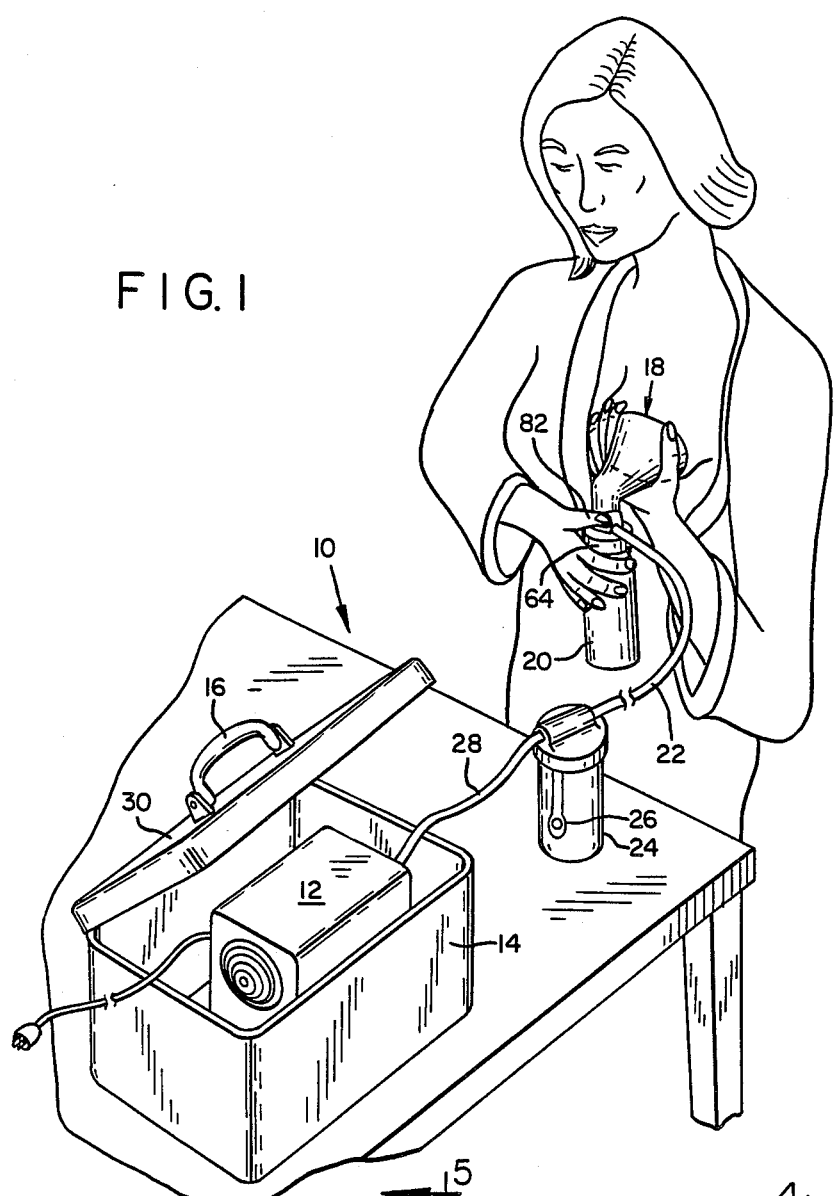
FIG. 1 is a pictorial view of a woman using a breast pump according to the present invention.
Figure 2:
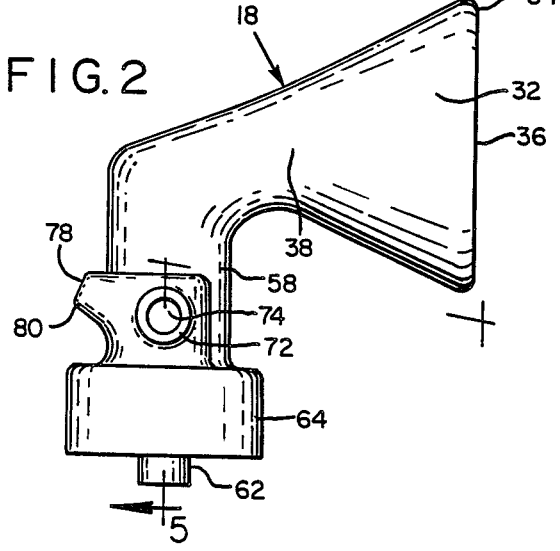
FIG. 2 is a side elevational view of the flexible flange of the breast pump shown in FIG. 1.
Figure 3:
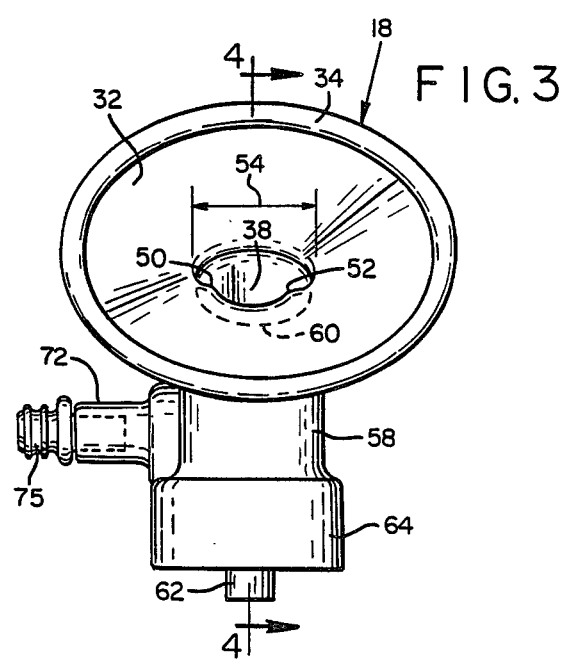
FIG. 3 is a front elevational view of the flexible flange shown in FIG. 2.

Referring now to the drawings, a breast pump 10 is shown in use in FIG. 1. A vacuum pump unit 12 is contained in a carrying case 14 equipped with a handle 16 permitting the entire breast pump 10 to be carried easily.

Preferably, the vacuum pump unit 12 is a lightweight pump driven by a small electric motor and capable of providing a vacuum of about 13-14 inches of mercury. The pump should have a displacement giving it a capacity to quickly provide a vacuum of that degree by evacuating any hose and the volume within any collection vessels within the system of the breast pump 10. It has been found that a compressor of 18 liter per minute displacement, manufactured by the Devilbiss Corporation of Somerset, Penn., as their model No. 7511, is satisfactory when connected for use as a vacuum pump. This vacuum pump unit 12 is small enough to fit conveniently within a small overnight case, leaving room for the additional components of the breast pump assembly 10.

A flange 18, which will be described in more detail subsequently, is held to the woman's breast to collect milk. The flange 18 is fastened atop a collection bottle 20 which receives the milk as it is delivered by the woman's breast. A vacuum hose 22, made of a material such as a medical grade silicone rubber, leads from the flange 18 to an overflow bottle 24. The overflow bottle 24 has a tight-fitting cover equipped to receive an end of the vacuum hose 22 to permit milk which overflows from the milk collection bottle 20 to flow into the overflow bottle 24. A ball check valve 26 equipped with a floating ball is provided within the overflow bottle 24 and connected to a pump vacuum hose 28 connected to the air inlet fitting (not shown) of the pump 12. The check valve 26 prevents milk from flowing into the pump 12 through the pump vacuum hose 28, should the woman fail to notice that milk has overflowed into the overflow bottle 24 from the collection bottle 20. This protects the vacuum pump unit 12 against damage.

The entire breast pump 10, including the pump unit 12, carrying case 14, flange 18, collection bottle 20, vacuum hoses 22 and 28, and overflow bottle 24, as described, weighs less than about 10 pounds, and, with the cover 30 of the carrying case 14 latched shut, the entire breast pump 10 can easily be carried by a woman for use in any convenient location where electrical power is available for the pump unit 12.

As may be seen more clearly in FIGS. 2–6, the flange 18 includes a conical mouth portion 32 which has a rounded lip 34 defining an outer end 36 of the mouth portion 32. The mouth portion 32 is elliptical as seen in front view (FIGS. 3, 5) and tapers inwardly to an inner end 38. The entire flange 18 is of a soft, flexible and resilient material, preferably a medical grade silicone rubber molded in the desired form. As may be seen in FIG. 4, the mouth portion 32 is defined by a wall 40 which tapers from a maximum thickness 42, adjacent the lip 34, to a minimum thickness 44, at the inner end 38. While the thicknesses 42 and 44 may vary, depending on the softness of the rubber used, it is important that the wall 40 be tapered so that the mouth portion 32 progressively squeezes against the breast as vacuum inside the flange increases.

A throat portion 46 of the flange 18 is generally tubular and extends at a downward angle, having its upper interior surface 48 extending generally parallel with the upper portion of the mouth 18.

The mouth portion 32 has a length between the outer end 36 and the inner end 38 which is great enough to receive a portion of a woman's breast with the nipple of the breast extending beyond the inner end 38 into the throat portion 46. For example, the length of the mouth portion 32 may be about 2 inches, while the length of the interior of the throat portion 46 is about 1¼ inches. Located along the lower interior surface of the throat portion 46 are a pair of elongate inwardly and upwardly protruding areas 50 and 52 which are spaced apart from and extend parallel to each other the shape of a baby's tongue, supported by its jaw, in order to provide as natural an interior contour as is practical within the flange 18. For example, the areas 50 and 52 may be ¼ inch wide, ¾ inch long, and protrude into the throat portion 46 about 3/32 inch.

This simulation of the shape of a baby's mouth is further enhanced by the throat portion 46 having a width 54 of about 1⅜ inches, while the interior height 56 of the throat is only about ⅝ inch.

The mouth and throat portions of the flange are supported by a vertically-extending neck portion 58, which has walls 59 at least about two to four times as thick as the minimum wall thickness 44 of the mouth portion 18.

From the lower end 60 of the throat portion, the interior width of the neck grows smaller, tapering toward and leading into a downwardly extending neck extension tube 62. Thus the wall thickness of the neck portion 58 is great enough to provide considerable rigidity of the neck portion 58, despite the entire flange 18 being of a soft silicone rubber in order for the mouth and the throat to be easily flexible.

A collar 64 extends outwardly from the neck 58 and thence downwardly about the neck extension tube 62, defining a bottle neck-receiving cavity 66 having a flat sealing surface 68, best seen in FIGS. 4, 5, and 6, surrounding the neck extension tube 62. A pair of inwardly-protruding ridges 70 are provided within the collar 64 to grip the normally-provided threads of the top of a conventional baby feeding bottle used as the collection bottle 20.

A hose connector receiver 72 extends laterally outwardly from the left side of the neck portion 58 and includes a bore 74 for receiving a hose connector 75 (FIG. 3) which may be of a hard plastic material. The bore 74 intersects a vent bore 76, which extends to a vent opening 78 defined in a vent neck 80. The vent neck 80 is directed rearwardly with respect to the mouth portion 32 and is located at the left side of the neck portion 58, approximately perpendicular to the hose connector receiver 72, so that a mother using the breast pump 10 can cover the opening 78 easily with her thumb 82 as shown in FIGS. 1 and 6.

Extending diagonally downward from the vent bore 76, and communicating between the vent bore 76 and an opening 84 defined in the horizontal sealing surface 68, is a vacuum bore 86. When the collection container 20 is located with its neck within the collar 64 the flat sealing surface 68 mates sealingly against the neck of the collection container 20. When the vacuum pump unit 12 is then energized and the vent opening 78 is closed, air will be drawn into the flange 18 through the mouth portion 32, throat portion 46, and downwardly through the neck 58 and neck extension tube 62 into the collection container 20, and thence outwardly through the opening 84, bore 86, and through the bore 74 of the hose connector receiver into the vacuum hose 22, as indicated by the arrows 94.

Figure 8:
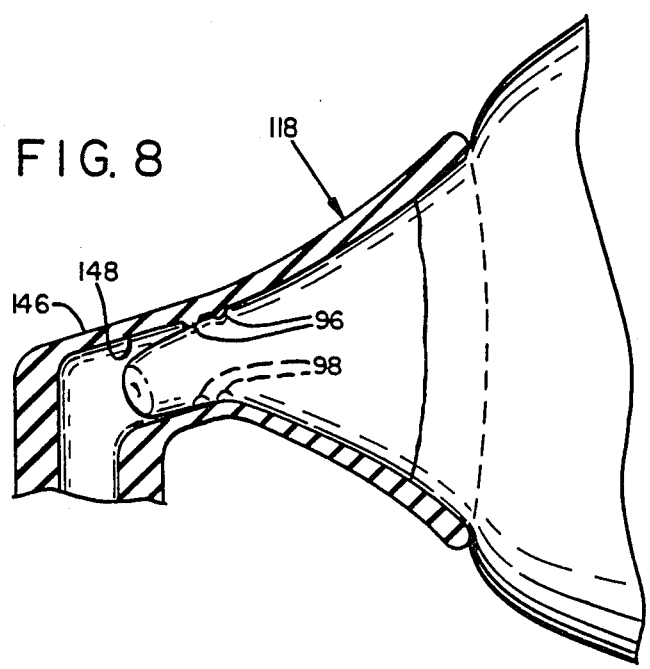
FIG. 8 is a view similar to that of FIG. 7 showing the alternative embodiment of a flange formed in accordance with this invention.

FIG. 8 depicts a cross-sectional view of an alternative embodiment of a flange 118 formed in accordance with this invention. Specifically, the flange 118 is substantially similar to the flange 18 described earlier with respect to FIGS. 2 through 6. In the embodiment shown in FIGS. 8 and 9, however, now upwardly protruding areas (reference numerals 50 and 52 in FIGS. 2–6) are included. Further, a pair of ridges 96 are itnegrally formed with the throat portion 146 to protrude from an infant's palate just behind the upper gums. Specifically, when an infant is suckling at the breast, the nipple is forced against the rugae, which act to anchor the nipple within the infant's mouth. The similarly shaped ridges 96 formed in the throat portion 146 of the flange provide the mentioned anchoring effect. Additionally, the presence of the ridges provide a natural sensation for the mother.

It is contemplated that the rugae-like ridges 96 need not be restricted to the upper interior surface 148 of the throat portion, for instance, the ridges may be extended (as shown in dotted lines of FIG. 8 at 98) to completely encircle the nipple to provide enhanced nipple-anchoring effect.

Figure 9:
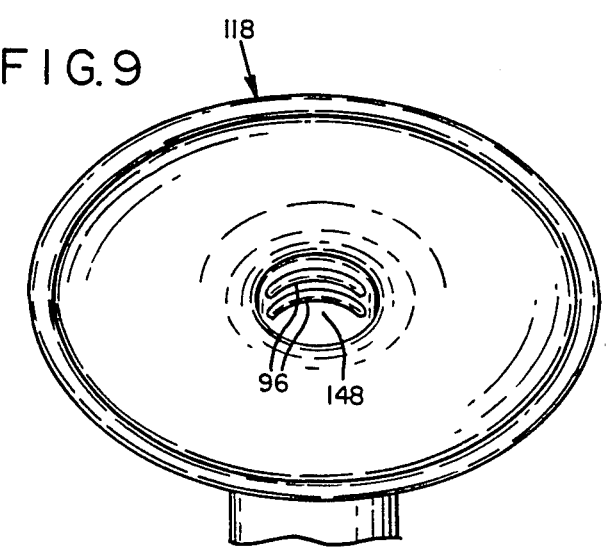
FIG. 9 is a front elevation view of the alternative embodiment of the flange.

Although only two ridges 96 are shown in the figures, more than two ridges may be employed. Further, the size of the ridges shown in FIGS. 8 and 9 are enlarged for clarity. In this regard, the ridges should protrude no more than 0.5 millimeters from the internal surface of the throat portion and have a radius of curvature of at least one millimeter.

To use the breast pump 10 of the present invention the collection bottle 20 and flange 18 are held by the woman, who places the nipple of her breast within the mouth portion 32, permitting the nipple to extend into the throat portion 46. When the vacuum pump unit 12 is actuated and the woman closes the vent opening 78, using a finger or the thumb 82, as shown in FIG. 6, air pressure, as indicated by the arrows 88, presses the flexible mouth portion 32 and throat portion 46, collapsing the wall 40 around the nipple 90, areola 92, and, depending upon the size of the woman's breast, a surrounding area of the breast, so that the breast is compressed by the flange at the same time suction is applied, simulating the action of a baby's mouth and natural sucking action.

When the woman feels that the milk which was previously present in the area surrounding the nipple 90 has been expressed from the nipple 90, she removes her thumb 82 from the vent opening 78, allowing air to enter through the vent bore 76 and vacuum bore 86, allowing air pressure within the collection container 20, neck portion 58 and throat portion 46 of the flange 18 to increase to equal the pressure surrounding the exterior of the flange 18. This permits the flange 18 and the breast to relax as shown in FIG. 7. Because of the soft, elastic nature of the wall 40 of the flange 18, the mouth portion 32 forms a seal against the skin of the woman's breast, holding the flange 18 in place on the woman's breast in much the same way in which a baby's mouth remains on the breast during natural breast feeding. This relaxation of the mouth portion 32 permits the sinuses of the breast to refill with milk as it is produced in the breast. The woman thereafter again closes the vent opening 78, again creating a vacuum within the collection container 20 and the flange 18. This cycle of closing and opening the vent opening 78 and thus providing suction and squeezing of the nipple 90 and surrounding area of the breast, followed by relaxation, is performed at a rate which is comfortable to the mother. Thus, once the milk has let down, a slow cycle may be used initially, while the flow of milk is quite large. Later, when most of the supply of milk has been removed from the breast, a quicker cycle may be more desirable.

When using the flange 18 in conjunction with a vacuum pump unit equipped with an automatic pulsator which controls the application and release of vacuum, the vent opening 78 is kept closed continuously. Alternatively, a small amount of air may be permitted to pass inwardly through the vent opening 78 to provide a smaller sucking force or entirely relieve the vacuum within the flange 18 and collection container 20.

Preferably, the woman holds the mouth portion 32 of the flange 18 against her breast, using the thumb and fingers of one hand both to massage her breast and to guide the collapse of the mouth portion 32, so that the wall 40 of the mouth portion 32 will collapse and squeeze the breast in the manner most similar to natural breast feeding by a baby. As a baby may often use its hands to squeeze its mother's breast during feeding, this massaging of the breast by the woman provides, together with the action of the flange, a very natural sensation, even though the mother's milk is being removed by the breast pump 10, rather than natural suckling by a baby.

As the wall 40 of the mouth portion 32 and throat portion 46 flexes, squeezing the breast, the elongate inwardly projecting areas 50 and 52 squeeze against the bottom of the breast, simulating the squeezing ordinarily performed by the baby's mouth in natural breast feeding. This squeezing performed by the mother and the flexing action of the flange 18 result in production of milk which is more natural in its content of protein and fat than milk which is obtained using suction and a hard flange such as those which have been used previously. Additionally, the soft elastic texture of the inner surface of the flange 18 results in a minimum amount of slippage and sliding of the flange 18 on the skin of the breast, and thus results in a significantly smaller amount of irritation of breast skin by use of the flange 18 than by use of a hard flange.

Using the flange 18 as described, a woman is able to drain the milk from her breasts in a shorter time, i.e. 10 to 12 minutes, and more completely and comfortably than with previous breast pumps, so that lactation can be prolonged to a period of several months with ample volume.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A breast pump flange for connection with a vacuum source, comprising:
   (a) a tubular throat portion having a wall defining an internal opening, the throat portion having opposing first and second ends, the first end of the throat portion being configured to receive a nipple within the internal opening;

(b) a conical mouth portion configured to receive a breast and having a resilient wall, the wall having an inner end contiguously connected with the first end of the throat portion and an outer end;

(c) vacuum connection means for connecting the second end of the throat portion to the vacuum source and selectively producing a vacuum within the internal opening of the throat portion; and (d) one or more ridges integrally formed with the throat portion near the first end thereof to protrude into the internal opening of the throat portion, the ridges oriented to at least partly encircled a nipple inserted into the throat portion.

2. The flange of claim 1 wherein the thickness of the mouth portion wall gradually increases along the length of the wall from the inner to the outer end.

3. The flange of claim 1 wherein the vacuum connection means includes venting means mounted proximal to the throat portion and operable for selectively venting the opening of the throat portion to the atmosphere.

4. The flange of claim 1 wherein the wall of the mouth portion has a smooth continuous external surface.

5. The flange of claim 1 wherein the ridges are annular shaped and oriented to completely encircle a nipple inserted into the throat portion.

* * * * *